US00PP14351P29

(12) United States Plant Patent
Ramirez

(10) Patent No.: US PP14,351 P2
(45) Date of Patent: Dec. 9, 2003

(54) COLEUS PLANT NAMED 'BALAUREVE'

(50) Latin Name: *Coleus×hybrida*
Varietal Denomination: Balaureve

(75) Inventor: Rolando Solano Ramirez, Dulce Nombre Cartago (CR)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/108,676

(22) Filed: Mar. 27, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Anne Marie Grünberg
(74) *Attorney, Agent, or Firm*—Wood, Phillips, Katz, Clark & Mortimer

(57) ABSTRACT

A new and distinct Coleus plant named 'Balaureve', characterized by its grayed-purple and green variegated leaves and vigorous upright bushy growth habit is provided.

1 Drawing Sheet

Latin name of genus and species of plant claimed: *Coleus×hybrida*.
Variety denomination: Balaureve.

BACKGROUND OF THE INVENTION

The present invention comprises a new and distinct Coleus plant, botanically known as *Coleus×hybrida* and hereinafter referred to by the cultivar name 'Balaureve'.

The new Coleus originated as the product of a controlled breeding program carried out in Cartago, Costa Rica during September 1997. The female (seed) parent of the new Coleus was the *Coleus×hybrida* variety 'Ducks Foot Camouflage' (not patented). The male (pollen) parent of the new variety was the *Coleus×hybrida* variety 'Mosaic Farway' (not patented). The new Coleus was discovered and selected as a single plant from within the progeny of the above stated cross during August 1998.

Asexual reproduction of the new cultivar by terminal tip or stem cuttings taken during 2001 in West Chicago, Ill., has demonstrated that the characteristics of the new cultivar as herein described are firmly fixed and are retained through successive generations of such asexual propagation.

SUMMARY OF THE INVENTION

It was found that the cultivar of the present invention:

(a) forms green and grayed-purple variegated leaves;

(b) exhibits an upright bushy form; and (c) exhibits a vigorous growth habit.

'Balaureve' has not been observed under all possible environmental conditions to date. Accordingly, it is possible that the phenotype may vary somewhat with variations in the environment, such as temperature, light intensity, and day length.

The new cultivar of the present invention can be compared to its female parent 'Ducks Foot Camouflage'. However, in side-by-side comparisons, the new Coleus exhibits a more branching habit and different leaf color.

BRIEF DESCRIPTION OF PHOTOGRAPH

The accompanying photograph shows, as nearly true as it is reasonably possible to make the same in color illustrations of this type, a typical plant of the new cultivar. The plants were grown for nine (9) weeks in a greenhouse at West Chicago, Ill.

DETAILED BOTANICAL DESCRIPTION

The chart used in the identification of colors described herein is The R.H.S. Colour Chart of The Royal Horticultural Society, London, England. The color values were determined on Nov. 21 , 2001, in West Chicago, Ill. The readings were taken between 10:00 and 11:45 p.m. under natural light conditions. The plants were produced from cuttings taken from stock plants and were grown in a double polycarbonate covered greenhouse under conditions comparable to those used in commercial practice. The plants were grown utilizing a soilless growth medium. Temperatures of approximately 75° to 85° F. (24° to 29° C.) during the day, approximately 60° to 70° F. (15° to 21° C.) during the night and light levels of 4,000 to 9,000 footcandles were maintained. The following measurements and descriptions were taken at nine (9) weeks after the planting of a rooted cutting.

Classification:
*Botanical.*—*Coleus×hybrida* cultivar 'Balaureve'.
*Commercial.*—Coleus.
Parentage:
*Female parent.*—'Ducks Foot Camouflage'.
*Male parent.*—'Mosaic Farway'.
Propagation:
*Type cutting.*—Terminal tip.
*Time to initiate roots.*—Approximately 10 to 14 days.
*Time to develop roots.*—Approximately 21 to 28 days.
*Root description.*—Fibrous and well branched.
Plant description:
*General appearance and form.*—Upright, bushy and vigorous.
*Crop Time.*—Four to five weeks are required to produce mature plant from rooted cuttings.

*Height from soil level.*—Approximately 13.3 cm. Width — Approximately 18.6 cm.

*Branching habit.*—Freely branching. Commonly forms approximately 3 main branches.

*Branch descriptions.*—Shape: Square in cross section. Length: Approximately 11.5 cm. Diameter: Approximately 5 mm. Color: 146B with streaks and areas at nodes of 187C. Surface: Densely covered with very short hairs. Length of longest Internode: Approximately 1.6 cm. Number of leaves per branch: Approximately 17.1.

Foliage description:

*Form.*—Mature foliage is simple.

*Arrangement.*—Opposite.

*Shape.*—Ovate.

*Margin.*—Lobed.

*Apex.*—Acute.

*Base.*—Attenuate.

*Venation pattern.*—Pinnate.

*Surface.*—Upper surface has very sparse pubescence. Lower surface is sparsely pubescent with moderate pubescence along veins.

*Color of young and mature foliage.*—Upper surface: Midvein and veins are 186B. Central portion of leaf is 184B with areas of 187A, occasional splotches and margin of 137C.

*Color of young and mature foliage.*—Lower surface: Midvein and veins of 138C with overlay of 186C. Background of 59A with occasional splotches of 138B.

*Size.*—Mature leaves are approximately 4.1 cm in length and approximately 2.4 cm in width.

*Petiole.*—Length is 2 cm. Diameter is 1 mm. Surface: Densely covered with very short hairs. Color is 138C with overlay of 186C.

Flower description: Flowers were not observed.

Seed production: Seed production has not been observed.

Disease resistance: Disease resistance has not been observed.

I claim:

1. A new and distinct cultivar of Coleus plant named 'Balaureve' substantially as herein shown and described, which:

(a) forms green and grayed-purple variegated leaves;

(b) exhibits a vigorous upright bushy growth habit; and (c) exhibits a vigorous growth habit.

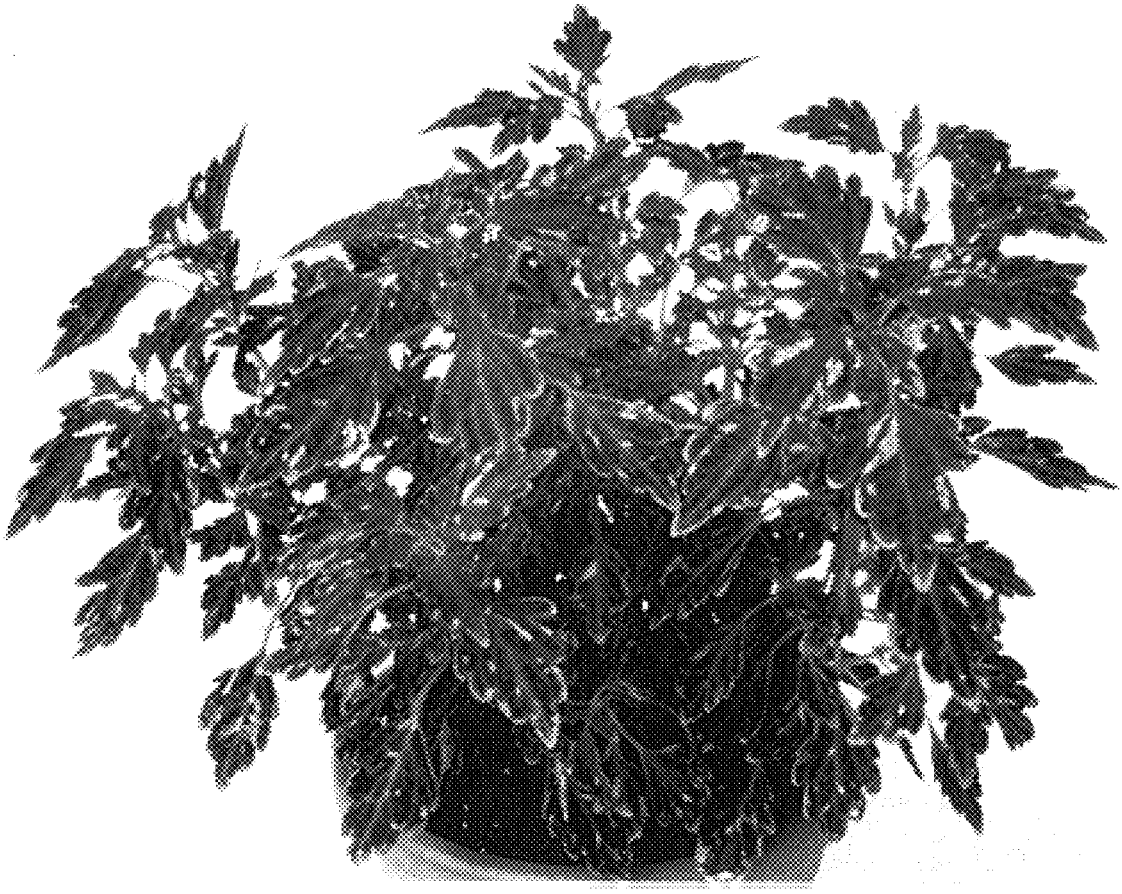

* * * * *